United States Patent [19]

Tao

[11] Patent Number: 4,687,997

[45] Date of Patent: Aug. 18, 1987

[54] CONTAINER WITH SAFETY FEATURES FOR CLEANSING MEDICAL DEVICES

[75] Inventor: Frank Tao, Sunnyvale, Calif.

[73] Assignee: CooperVision, Inc., Mountain View, Calif.

[21] Appl. No.: 623,401

[22] Filed: Jun. 22, 1984

[51] Int. Cl.⁴ ............................................. G01N 27/02
[52] U.S. Cl. ...................................... 324/439; 422/28; 134/143; 204/32.1
[58] Field of Search ................ 324/425, 439–450; 422/30, 28; 134/143; 204/32.1, 286, 242

[56] References Cited

U.S. PATENT DOCUMENTS

| | | | |
|---|---|---|---|
| 3,849,723 | 11/1974 | Allen | 324/446 |
| 3,938,035 | 2/1976 | Fletcher | 324/450 |
| 4,047,100 | 9/1977 | Robinson | 324/442 |
| 4,055,797 | 10/1977 | Doeleman | 324/442 |
| 4,156,179 | 5/1979 | Stephen | 324/442 |
| 4,206,407 | 6/1980 | Bender | 324/449 |
| 4,265,727 | 5/1981 | Beckley | 204/242 |
| 4,369,104 | 1/1983 | Beckley | 204/286 |
| 4,496,906 | 1/1985 | Clack | 324/439 |

Primary Examiner—Michael J. Tokar
Attorney, Agent, or Firm—Vorys, Sater, Seymour and Pease

[57] ABSTRACT

A system for measuring the electrical conductivity of disinfecting and rinsing solutions within a cleansing container includes a power supply for driving a pair of detectors and/or a meter, a conductivity probe for measuring the electrical conductance of the solutions, an oscillator, amplifier, and rectifier circuit, and indicators such as colored lights for indicating the type of solution within the container. The entire measuring system may be miniaturized and provided within the lid of the container. The system is particularly adapted to ensure that the correct steps are taken during the disinfection of contact lenses.

24 Claims, 2 Drawing Figures

U.S. Patent  Aug. 18, 1987  4,687,997
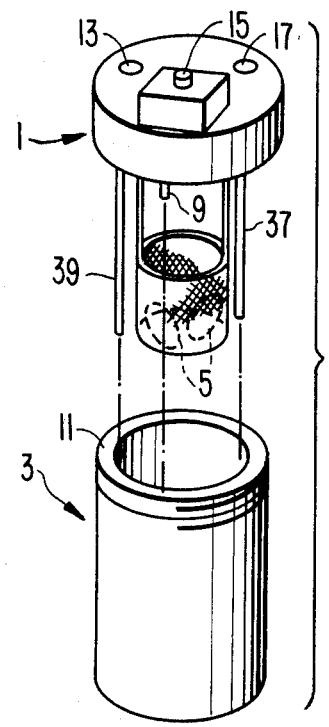
FIG. 1.
FIG. 2.
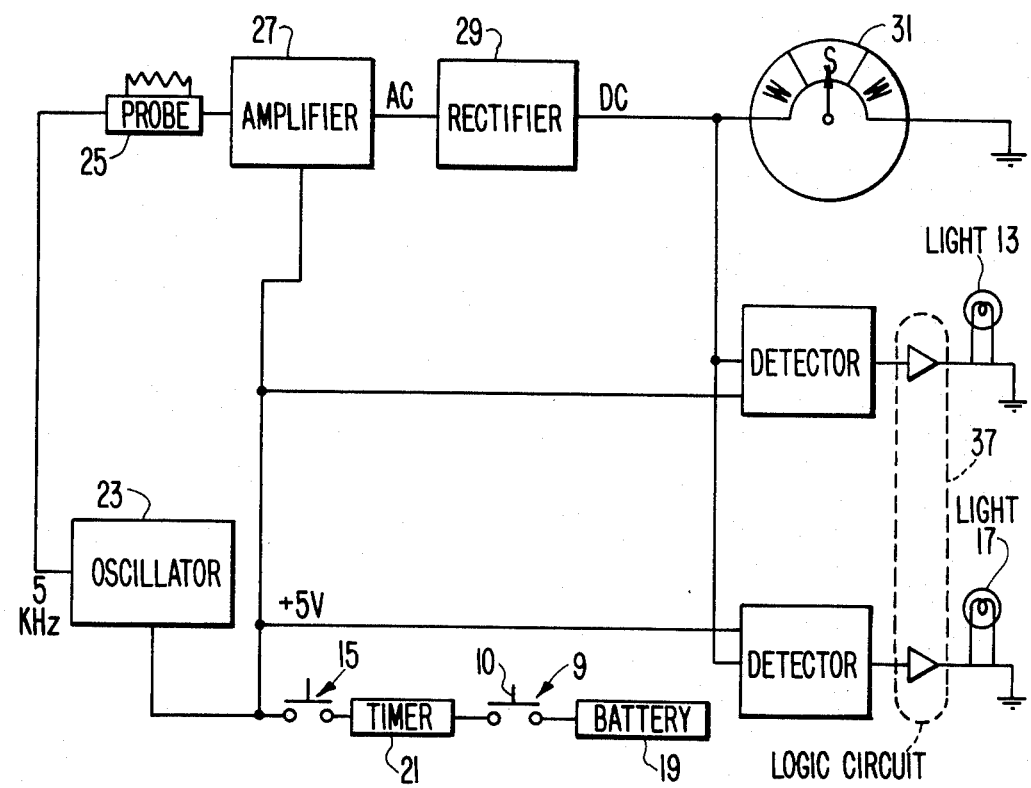

4,687,997

CONTAINER WITH SAFETY FEATURES FOR CLEANSING MEDICAL DEVICES

BACKGROUND OF THE INVENTION

1. Field of the Invention

This invention generally concerns a container into which articles employed in medical applications are placed for sterilization and further concerns a container designed to ensure that proper steps are taken during a disinfecting regimen. More particularly, this invention deals with the use of the electrical conductivity of aqueous disinfecting solutions or any other electrolytic solutions used for removing residuals that may be harmful to living tissues from surfaces of the articles.

2. Description of the Prior Art

There are many disinfecting agents available for use in aqueous solutions. Some of the well-known germicidal agents are hydrogen peroxide, thimerosal, chlorohexidine, glutaraldehyde, alcohols, and inorganic salts. The concentrations of these agents range from about 0.001% to 30% or more. Some of these solutions may contain ionic salts to maintain a certain tonicity in order to be compatible with the physiological fluids.

Normally a second solution is used in combination with the disinfecting solution during a disinfecting regimen. The second solution may include distilled water, saline or other solutions containing agents specific for interaction with a particular disinfectant. The purpose of the second solution usually is to remove, neutralize or decompose excess germicidal agents remaining on the articles after the disinfection step. This can be accomplished simply by physical removal, or by reacting the disinfecting agent chemically or physically such that the final products are rendered harmless to living tissues. The second solution is usually called a neutralizing agent. The concentrations of this solution usually depend on the concentrations of the disinfectant used.

Germicidal agents are used to sterilize such articles and devices as surgical tools, contact lenses, dental appliances, catheters, syringes, and packaging materials. Any residual amount of the germicidal agent remaining after treatment may require removal depending on the affects of the agent upon living tissue. For example, in cases where the application of the article or device containing residual amounts of germicidal solution may cause cellular damage or, at the very least, a significant amount of irritation to the patient or user, the germidical agent must be removed.

A specific case in point is the disinfection of soft contact lenses with hydrogen peroxide. This method of disinfection is a common practice for contact lens wearers. Hydrophilic soft contact lenses may contain up to 80% water and therefore absorb or even concentrate hydrogen peroxide within the lens matrix. After the disinfecting step, residual hydrogen peroxide must be removed before insertion of the lenses into the eyes as hydrogen peroxide will adversely react with the eye tissue and this is usually accomplished by treating the lenses with a neutralizing solution.

A problem associated with the such systems is that it is very easy for a patient to forget which solution is in the cup. Moreover, the patient may accidentally use the wrong sequence of solutions in the disinfection regimen. For example a neutralizing solution may be mistakenly used initially and followed by a hydrogen peroxide solution.

Thus, there exists the need for a cleaning system for contact lenses which alerts the user to the presence of harmful cleaning agents and which informs the user when a proper cleaning sequence has been completed.

SUMMARY OF THE INVENTION

Accordingly, this invention has been made to overcome the problems described above, and therefore has an object to provide a container which will prevent the above-noted errors and will ensure that the patient has taken the correct steps in disinfecting contact lenses and has properly neutralized any residual hydrogen peroxide before inserting the lenses within the eyes.

Another object of the invention is to provide a sterilizing container adaptable for use with thermal disinfection systems.

Yet another object is to inform a patient or user if the proper solution such as a saline solution and/or the correct volume of such solution was used during disinfection. One such example would be in a situation where the patient normally uses salt tablets dissolved in distilled water to thermally disinfect lenses. If the patient forgets to add the salt tablets or adds too many tablets the system will provide a warning signal immediately after submerging the lenses in the solution to warn of an improper solution concentration.

Still another object is to warn a patient or user when insufficient solution has been added to the container and/or to warn when the solution level in the container has decreased due to leakage of the container.

A further object is to provide a visual signal indicating when the proper time period for both disinfection and neutralization has elapsed.

The foregoing and other objects are achieved according to the present invention through the use of the electrical conductivity properties of the above-noted disinfecting and neutralizing solutions. A system for measuring electrical conductivity in the disinfecting container or case may include a power supply for driving detectors and/or a meter; a conductivity probe for measuring the electrical conductance of the solutions; as oscillator, amplifier, and rectifier circuit as a current source; a detector and/or meter circuit as an indicator of conductance; a case for holding the solution; and a cover for the case.

The energy source for this system can be either a battery or power from AC household current. The electrodes of the conductivity probe can be constructed out of any electrically conductive material that is compatible with the solution in question. For example, if hydrogen peroxide is used as a disinfectant, the probe material may be of aluminum, tin or other metals that do not catalyze the decomposition of peroxide. The indicator can be either a meter with a scale and needle, a digital meter or a plurality of lights of different colors.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts through the several views and wherein:

FIG. 1 is a perspective view of the case and lid, partly in section, showing the location of the electronic detection system within the container lid; and FIG. 2 is schematic block diagram of the electronics provided within the container lid.

DETAILED DESCRIPTION OF THE PREFERRED EMBODIMENTS

The apparatus developed in accordance with the present invention will now be described in conjuction with the drawings wherein a device is provided for measuring and indicating a difference in the electrical conductivity of disinfecting solutions and neutralizing solutions to ensure that a prescribed disinfecting regimen has been properly conducted. Where hydrogen peroxide is used as a disinfectant and is subsequently neutralized with a neutralizing solution, the difference in electrical conductivity between the two solutions is indicated by either a meter or by a pair of different colored lights to indicate and identify the presence or absence of each solution. The ionic strength of the hydrogen peroxide is typically much lower than that of the neutralizing solution. This difference can be used advantageously to monitor the disinfecting process.

More particularly, the ionic strength of the neutralizing solution is such that it is compatible or isotonic with human serum and tear fluid. That is to say, the salt concentrations of these neutralizing solutions are such that they are nearly equal to those present in serum or tear fluid. The normal ionic strength of the serum or tear fluid exhibits a tonicity of 285-310 milliosmoles/kg, which is equivalent to about 9 milligrams of sodium chloride per milliliter of fluid. The present invention takes advantage of the salt contents of these neutralizing solutions and, if necessary, gives a warning to the user of any impending danger due to misuse of the solutions.

A specific example according to the invention uses a container or case for disinfecting hydrophilic soft contact lenses with hydrogen peroxide. A subsequent neutralization of the hydrogen peroxide with sodium pyruvate is carried out. The entire process is monitored and evaluated as set forth below.

The germicidal agent, hydrogen peroxide, is normally in solution at a concentration of 30 mg/ml and may contain trace amounts of stabilizers, i.e., phenacetin, sodium stannate, sodium pyrophosphate, and sodium nitrite. The conductance of such solution is 250 $\mu$mhos/cm. The dissociation constant of hydrogen peroxide, $1.78 \times 10^{-12}$ @20° C., is slightly greater than that of water. The only other sources of ions in commercial hydrogen peroxide are the stabilizers which are added in trace amounts.

The neutralizing solution has the following composition:

|  | mg/ml |
| --- | --- |
| Poloxamer 407 | 10.0 |
| Sodium Chloride | 2.0 |
| Potassium Chloride | 1.0 |
| Sorbic Acid | 2.0 |
| Sodium Borate | 2.2 |
| Edetate Sodium | 1.0 |
| Boric Acid | 10.0 |
| Sodium Pyruvate | 5.0 |
| Purified Water | Q.S. |

The conductance of this neutralizing solution is 5,500 $\mu$mhos/cm.

An example of the case used for containing the above solutions is illustrated in FIG. 1. The electronic components to be described below will preferably be housed in the lid 1, for example, within housing 2. The solutions will be contained in the case 3.

After completing the proper initial cleansing steps, the articles to be disinfected such as lenses 5 are placed in a basket 7 attached to the lid 1 of case 3. The case 3 is then filled with hydrogen peroxide, usually 10 cc. When the case 3 is closed with the lid 1, a switch mechanism 9 activates a timer 21 shown in FIG. 2. The action of turning or rotating the lid 1 to secure it onto the case 3 causes the switch 9 to ride against the wide lip 11 of the case 3, thereby depressing switch 9 via a sliding camming action. Timing mechanism 21 is preferably housed within lid 1. Of course a simple snap fit or bayonet coupling rather than the threaded engagement between the lid 1 and the case 3 may be used, as well as any other well-known connection.

Normally, disinfection takes 10 minutes. During this period a signal such as a steady light 13 may be displayed whenever button 15 is depressed to indicate the presence of peroxide. Light 13 rather than light 17 will illuminate because the lower electrical conductivity of the hydrogen peroxide solution than that of the neutralizing solution will be detected and used to select the illumination of one of the pair of indicators lights, 13 and 17. The electronic logic to be discussed below will identify a solution by its conductivity and cause the appropriate light 13, 17 to illuminate or to provide power to a switch 15 which operates such light. The purpose of button switch 15 is to conserve energy, especially when disposable batteries are used for an energy source. Of course, button switch 15 is optional such that a constant power supply may be fed to lights 13 and 17.

After the 10 minute disinfection period, or any other predetermined disinfection period programmed or preset into timer 21, light 13 will begin to blink when the button switch 15 is depressed to indicate that the proper time has elapsed for adequate disinfection. This provides an indication to the user that the next cleaning step should begin, namely the neutralizing step. Timer 21 includes a standard circuit for generating an intermittent signal whenever a predetermined period of disinfection or neutralization has been completed such as the 10 minute period noted above. This signal will cause light 13 or 17 to blink on and off.

After the disinfection period is completed the lid 1 is unscrewed or removed from the case 3 so that switch 9 opens thereby causing the timer 21 to be reset to zero in a conventional known manner. After discarding the hydrogen peroxide solution, the case 3, lid 1 and basket 7 are rinsed with neutralizing solution. After discarding this rinse solution, the case 3 is refilled with neutralizing solution for the neutralizing step and the lid 1 is replaced.

Securing the lid 1 to the case 3 causes the timer 21 to be activated again. This time however, because of the higher conductance of the neutralizing solution, light 17 will be lit when switch button 15 is depressed rather than light 13. Thus, light 17 indicates the presence of neutralizing solution. After a lapse of, for example, 10 minutes, depressing the button 15 will cause light 17 to be displayed as a blinking light indicating an adequate period has elapsed. The lenses 5 are now ready to be worn by the user.

The circuitry required to carry out the invention is schematically depicted in FIG. 2 wherein a power source is shown as battery 19 which is connected to timer 21 via switch 9. The plunger 10 of switch 9 is actuated as indicated above by contact with the lip 11 of case 3 to start the timer 21. Removal of lid 1 will automatically reset the timer 21 to zero. The timer 21 may be designed to provide a steady output from battery 19 during an initial disinfection period, such as the 10 minute period described above. After this initial period the timer may be preset to provide an intermittent output so that either light 13 or 17 will be intermittently actuated to provide a blinking effect depending upon the conductivity of the solution within case 3. As noted above, switch 15 is optional and may be omitted such that a steady power output from battery 19 is available at all times to lights 13 and 17 and such that a logic circuit discussed below will determine which light will be lit.

An oscillator 23 receives power directly from battery 19 which provides a steady voltage of, for example, 30 5 volts to oscillator 23 as shown. Oscillator 23 is designed to convert the DC power from battery 19 to AC power having a frequency of, for example, 5 kHz. The alternating current from oscillator 23 is supplied to conductivity probe 25 having spaced electrodes which become immersed in a solution within case 3 upon closing of lid 1. Alternating current is preferred to operate probe 25 to prevent polarization of the electrodes and electrolysis of the solution.

Probe 25 provides a signal proportional to the conductivity of the solution within which it is immersed. This signal is amplified by amplifier 27 and fed to rectifier 29 to convert the AC signal to a DC signal suitable for input into meter 31 and/or conductivity detectors 33 and 35. The detectors may take the form of any conventional device for detecting the electrical signal level from amplifier 27 such as a comparator or Schmitt trigger device. Thus, meter 31 will offer a quantitative or qualitative reading over a continuous scale via a needle pointer or digital scale representative of the conductivity of the solution in case 3, while detectors 33 and 35 will provide inputs to logic circuit 37 which will determine whether light 13 or 17 will be illuminated. The detectors may be adjustable to accommodate their sensitivities to different solutions having different conductivities.

Instead of relying on timer 21 to trigger a blinking signal indicating that sufficient time had elapsed for a particular step, it may be possible to establish a threshold conductivity so that, for example, signal light 13 will remain illuminated until the disinfectant has dissipated to a preset concentration level if the conductivity of the neutralizing solution changes significantly during the neutralizing step. At this time the threshold conductivity will be exceeded and signal light 13 will be extinguished by logic circuit 37 while at the same time signal light 17 will be illuminated to indicate that the disinfectant has been adequately neutralized. Light 13 may be designed as a red light to indicate a warning signal, while light 17 may be designed as a green light to indicate a safety signal. Thus, probe 25 will send a constant signal to detectors 33 and 35 which will in turn provide logic circuit 37 with a further output signal corresponding to the electrical conductance of the solution. The signals from detectors 33 and 35 will change value at the predetermined threshold value so that one light will extinguish while the other illuminates.

In a preferred embodiment the sensitivity of the probe 25 is adjusted or set in accordance with the conductivity of the hydrogen peroxide disinfecting solution so that the conductivity of such solution is sufficient to generate an adequate output from probe 25 and to maintain light 13 in an illuminated state during the disinfection step. If too weak or too strong a solution is used, the detectors 33, 35 may be arranged to prevent illumination of one or both lights.

The sensitivity of probe 25 may be adjusted so that the conductivity of the disinfecting solution is sufficient to generate an adequate signal to cause light 13 to illuminate during the disinfecting step and further adjusted so that the conductivity of the neutralizing solution is sufficient to cause light 17 to illuminate during the neutralizing step. If the wrong type of solution is used, a warning signal may be provided by meter 31 indicating the presence of a conductivity outside the range of that representative of the correct solution. For example, the scale of meter 31 may be marked to indicate an acceptable range of conductivity within the middle of the scale. Readings on the extreme high end and low end of the scale would then be labeled as unacceptable, thereby warning the user of a potential problem such as the presence of solutions having inadequate or excessive strengths.

Instead of relying on meter 31 to provide a warning signal, detectors 33 and 35 may be set to provide a warning signal by illuminating lights 13 and/or 17 upon detecting a conductivity outside an acceptable range. For example, should a disinfecting solution require salt tablets, the detectors can be arranged to generate a warning signal via lights 13 and/or 17 if too few or too many tablets are added, as the resulting conductivity will lie outside an acceptable predetermined range programmed into detectors 33 and 35. Of course, a third detector and a third light could be provided to signal the presence of an excessive solution concentration.

It is also possible to provide a warning signal to the user in the case where an insufficient quantity of solution is present in case 3. This is accomplished by disposing probe 25 within lid 1 so that its electrodes will extend into the solution to a point below which an insufficient quantity solution is considered to be present. Thus, when the level of solution falls below probe electrode 37 or 39, a negligible conductivity will be present such that an alarm signal will be generated in the same manner as in the case where insufficient tablets have been dissolved in the solution.

An alternative design fixes the probe electrodes against or partially within the inner wall of the case 3 for connection with the probe and associated electronics upon closure of lid 1. These electrodes would be positioned at a preset level above the bottom of the case 3 to provide a signal indicating the presence of insufficient solution within case 3.

It is of course possible to incorporate the conductivity sensing elements of the invention in the bottom of the case 3 without detracting from the objective of this invention.

Obviously, numerous modifications and variations of the present invention are possible in light of the above teachings. It is therefore to be understood that within the scope of the appended claims, the invention may be practiced otherwise than as specifically described herein.

I claim:

1. A system for cleansing medical devices comprising:
   a containing means in which the medical device is positionable,
   disinfecting solution positionable in said containing means for disinfecting therein the medical device, an indicating means for indicating that the medical device as been subjected to said disinfecting solution in said containing means for a sufficient period of time, and neutralizing solution in which the medical device is positionable, after said indicating means has indicated sufficient time, for neutralizing on the medical device the residual of said disinfecting solution.

2. The system of claim 1 including,
said disinfecting solution including hydrogen peroxide.

3. The system of claim 1 including,
a measuring means for measuring the electrical conductance of the liquid contents of said containing means.

4. The system of claim 3 including,
an electronic logic means for distinguishing between said disinfecting solution and said neutralizing solution based on the conductance measured by said measuring means.

5. The system of claim 3 including,
a conductance indicating means for indicating the conductance measured by said measuring means.

6. The system of claim 5 including,
said conductance indicating means including at least one light.

7. The system of claim 5 including,
said conductance indicating means including a meter.

8. The system of claim 5 including,
said conductance indicating means including a warning signal indicating when the electrical conductance is outside of an acceptable range.

9. The system of claim 5 including,
said conductance indicating means including a signaling means for signaling when an insufficient volume of solution is present in said containing means.

10. The system of claim 1 including,
said medical device including a hydrophilic soft contact lens.

11. The system of claim 1 including,
said disinfecting solution having its ionic strength being less than that of said neutralizing solution.

12. The system of claim 1 including,
said neutralizing solution comprising sodium pyruvate.

13. The system of claim 1 including,
said indicating means including a timing mechanism.

14. The system of claim 13 including,
a lid connectable to said containing means, and
said timing mechanism being activated when said lid is connected to said containing means.

15. The system of claim 13 including,
a basket depending from said lid for holding said medical device in said containing means.

16. The system of claim 15 including,
said timing mechanism being housed in said lid.

17. An apparatus for treating contact lens in a disinfecting solution comprising:

a container for containing the disinfecting solution,
said container including a cup and a lid,
a basket depending from said lid, positionable in said cup, and adapted to hold at least one contact lens in the disinfecting solution,
a measuring means positioned in said lid for measuring the electrical conductance of the solution in said container and generating a signal corresponding to the conductance,
a switch means disposed in said lid for connecting said measuring means to a power supply,
an indicating means responsive to said signal for indicating the conductance, and
a timing means activated by said switch means for timing the treatment of the contact lens in the disinfecting solution.

18. The apparatus of claim 17 including,
said indicating means including an electronic logic means for identifying the presence of a solution in said cup having generally the same conductance as the disinfecting solution.

19. A method for cleansing a medical device comprising:
placing the medical device and disinfecting solution in a container to generally begin the disinfecting step for the medical device,
measuring the electrical conductance of the disinfecting solution in the container,
thereafter, removing the disinfecting solution from the container after an automatic indicator means connected to the container has indicated the end of the disinfecting step,
thereafter, placing neutralizing solution in the container to begin the neutralizing step for the medical device, and
removing the medical device from the container after the completion of the neutralizing step.

20. The method of claim 19 including,
after said neutralizing solution placing step, measuring the electrical conductance of the neutralizing solution in the container.

21. The method of claim 19 including,
said device placing step including placing the medical device in a basket and positioning said basket in said container.

22. The method of claim 19 including,
activating said automatic indicator means by fitting a lid on said container and thereby actuating a switch of said automatic indicator means.

23. The method of claim 19 including,
after removing the disinfecting solution and before placing neutralizing solution in the container, rinsing the container.

24. The method of claim 19 including,
said placing including said medical device being a soft contact lens and said disinfecting solution being hydrogen peroxide.

* * * * *